United States Patent [19]
Fields

[11] Patent Number: 5,692,235
[45] Date of Patent: Dec. 2, 1997

[54] RECURVE VISOR

[75] Inventor: Kyle D. Fields, El Dorado Hills, Calif.

[73] Assignee: Op-D-Op, Inc., Roseville, Calif.

[21] Appl. No.: 591,033

[22] Filed: Jan. 25, 1996

[51] Int. Cl.$^6$ ....................................................... A42B 1/06
[52] U.S. Cl. ......................................................... 2/12
[58] Field of Search .................................. 2/12, 13, 426, 2/427, 431, 438, 439, 442, 445, 448, 449, 450, 451, 452, 436, 437; 351/114, 62, 111, 113, 123

[56] References Cited

U.S. PATENT DOCUMENTS 2,642,568  6/1953  Stewart ........................................ 2/436
4,815,838  3/1989  Liataud ........................................ 2/12
4,916,754  4/1990  Kang ............................................ 2/12
5,046,192  9/1991  Ryder ........................................... 2/12

Primary Examiner—C. D. Crowder
Assistant Examiner—Larry D. Worrell, Jr.
Attorney, Agent, or Firm—John P. O'Banion

[57] ABSTRACT

A head worn visor with a headband, a forwardly disposed bill attached to the headband, a pair of rearwardly disposed outer arms coupled to the headband, and a pair of recurve arms attached to the outer arms by resilient hinge regions such that the recurve arms are spaced apart from the outer arms and provide a gripping surface for the wearer's head.

15 Claims, 2 Drawing Sheets 5,692,235

RECURVE VISOR

BACKGROUND OF THE INVENTION

1. Field of the Invention

This invention pertains generally to visors, shades, shields, and other head-worn devices, and more particularly to a head visor for increased wearer comfort having elongated arms, coupled to a headband, which recurve inward through a resilient hinge region to arcuate inner head gripping segments.

2. Description of the Background Art

Visors having forwardly disposed bills are commonly used to shade a wearer's eyes from sun or overhead room lights. Such devices are popular with joggers, golfers, tennis players, and other persons engaged in outdoor sports activities to prevent sunburn and reduce glare. Visors are also commonly used in laboratories, machine shops, and in medical and dental practices for supporting or suspending head-worn gear. For example, in the medical, veterinary, and dental professions, implements such as lights, reflectors, magnifying optics, and protective face shields are suspended from head visors to aid the wearer during work.

A common deficiency with presently known head worn visors is that they are uncomfortable to wear for extended periods of time. Many visors employ a resilient headband with a pair of side members that tensionally engage a wearer's head. Another common arrangement involves a head encircling band or strap, generally of resilient material, with circumferential adjustment means in a rearwardly disposed location. Common adjustment means include snap-tab arrangements, tie strings, pile fabric and fastening hook arrangements such as VELCRO®, buttons, and buckle-type fasteners. The aforementioned visor configurations, however, tend to result in wearer discomfort and require occasional repositioning or adjustment by the wearer to increase comfort. In many situations, the wearer cannot readily adjust the position of the visor to make it more comfortable on the wearer's head because both of the wearer's hands occupied, thus exacerbating the discomfort.

A frequent source of the discomfort experienced with head worn visors is due to perspiration associated with the portion of the headband or strap which covers the hair of a wearer, generally along the sides of a wearer's head. Such discomfort is particularly pronounced in the case of persons with long and/or thick hair. This discomfort can be partially alleviated by placing the hair outside of the headband or strap. However, even when worn on the outside of a headband, hair provides good thermal insulation, and thus wearers of head visors still tend to experience discomfort due to perspiration.

Accordingly, there is a need for a head worn visor which is comfortable to wear for extended periods of time, and which reduces the discomfort associated with perspiration. The present invention satisfies these needs, as well as others, and generally overcomes the deficiencies found in the background art.

SUMMARY OF THE INVENTION

The present invention pertains to a head worn visor which provides for increased wearer comfort. In general terms, the invention comprises a headband, a forwardly disposed bill or shade attached to the headband, a pair of outer support arms, and a pair of inner head gripping recurve arms or segments, with each inner recurve arm coupled to one of the outer support arms by a resilient hinge or fold region.

By way of example and not of limitation, the inner recurve arms are spaced apart from each other to accommodate a wearer's head therebetween. The inner recurve arms preferably are spaced apart from and generally parallel to their respective support arms, with each recurve arm including a forwardly disposed tip. The hinge or fold regions which join each the recurve arms to the support arms comprise generally U-shaped portions so that the recurve arms have a generally folded or curved back appearance relative to the arms. The recurve arms preferably have a slightly curved head gripping region which is structured and configured to comfortably engage a wearer's head.

In using the invention, the head gripping regions of the recurve arms contact the wearer's head, while the outer support arms provide tensional force to the recurve arms and head gripping regions through the resilient hinge or fold regions. This arrangement spreads the force exerted on the wearer's head by the arms over a relatively large area provided by the head gripping regions of the recurve arms, thereby retaining the head visor on the head of the wearer in comfortable fashion.

An object of the invention is to provide a head visor which is comfortable to wear for extended periods of time.

Another object of the invention is to provide a head visor which does not require circumferential adjustment to accommodate different users.

Another object of the invention is to provide a head visor which holds the hair of the wearer away from the wearer's head.

Another object of the invention is to provide a head visor which is simple and inexpensive to manufacture.

Another object of the invention is to provide a head visor which is aesthetically appealing.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
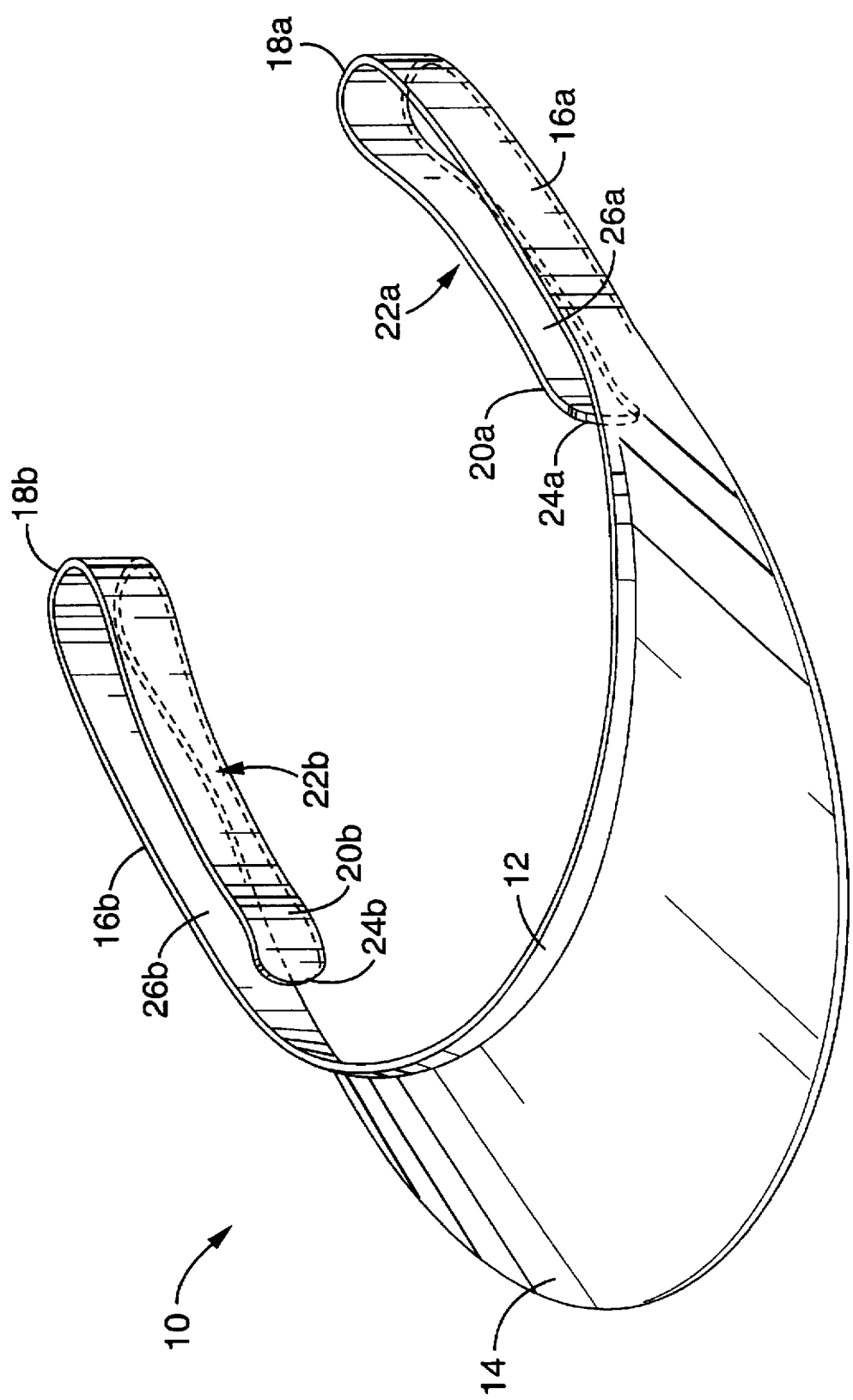
FIG. 1 is a perspective view of a recurve visor in accordance with the present invention.
Figure 2:
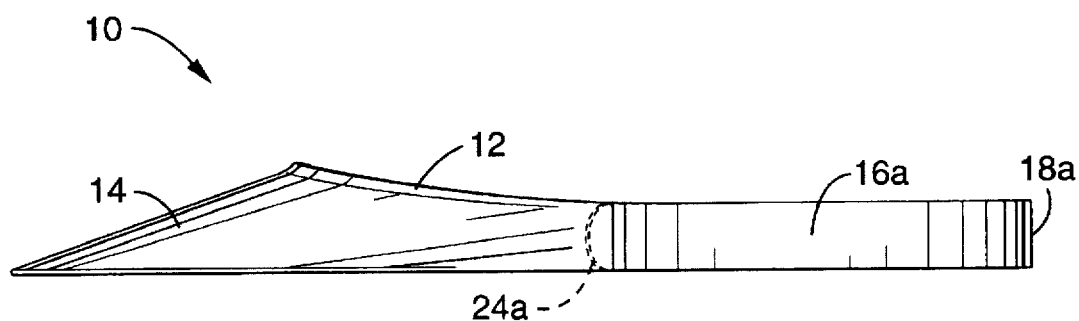
FIG. 2 is a side view of the apparatus shown in FIG. 1.
Figure 3:
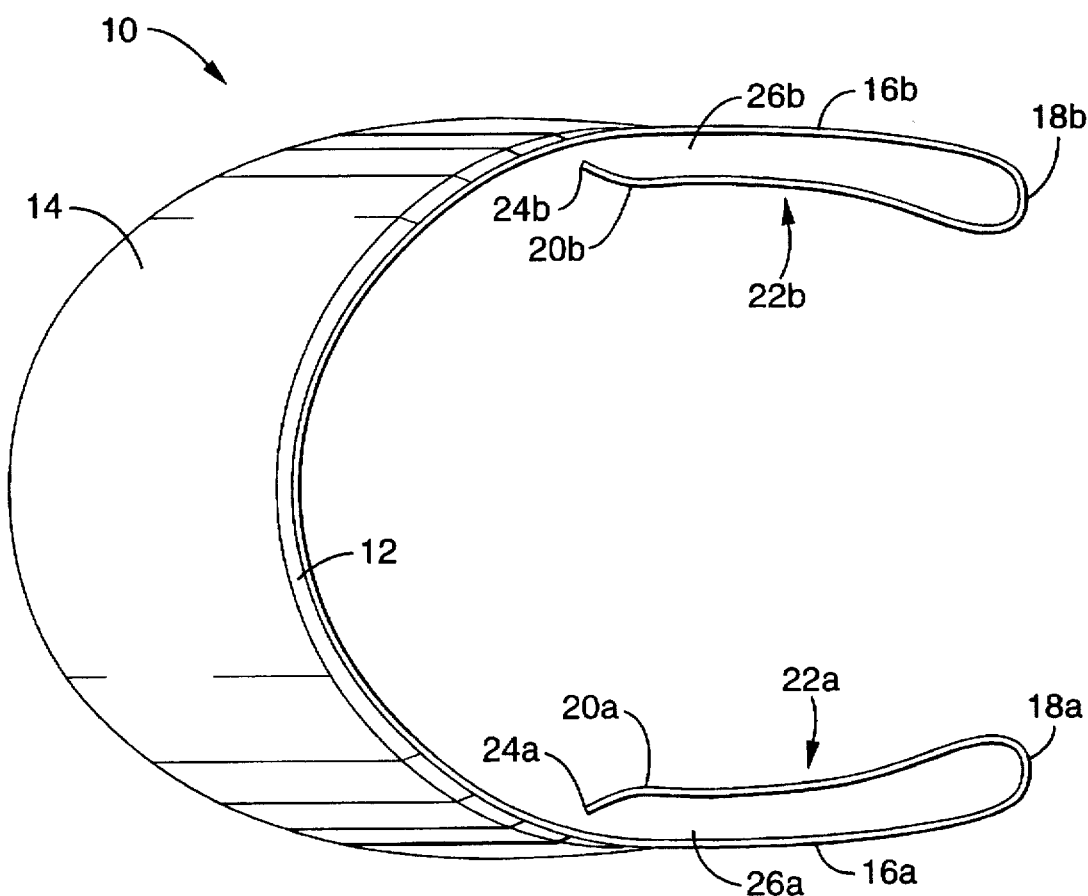
FIG. 3 is a top plan view of the apparatus shown in FIG. 1 and FIG. 2.

Referring more specifically to the drawings, for illustrative purposes the present invention is embodied in the apparatus which is generally shown in FIG. 1 through FIG. 3. It will be appreciated that the apparatus may vary as to configuration and as to details without departing from the basic concepts as disclosed herein.

Referring now to FIG. 1 through FIG. 3, a recurve visor 10 in accordance with the present invention is generally shown. Visor 10 includes a generally curved or arcuate headband 12 which is structured and configured to partially encircle the head of a wearer. Headband 12 is preferably made from a resilient, polymeric material. A forwardly disposed bill or shade 14 is coupled to headband 12. Bill 14 may be varied in size and shape according to need, and generally serves to provide shade to a wearer in order to reduce glare to the wearer's eyes, and to prevent sunburn from occurring on a wearer's face. Bill 14 may be integral to headband 12 and fabricated from the same material as headband 12, or bill 14 may alternatively be a separate piece which is fastened or attached to headband 12 by conventional means such as stitching, adhesives or the like. Bill 14 may also serve as a support for various devices such as protective face shields, lights, magnifying optics, and like items which are used in medical, dental, and other clinical professions.

First 16a and second 16b outer support arms are connected to headband 12, and extend from headband 12 in a generally rearward direction, such that the arms are rearwardly disposed relative to bill 14. Support arms 16a, 16b are preferably resilient in nature and are spaced apart to fit around a wearer's head. Further, support arms 16a, 16b are preferably structured and configured so as to oppose each other in a pincer-like arrangement as shown, so that tensional force is applied to a wearer's head by first and second support arms 16a, 16b to retain head visor 10 onto a wearer's head, as discussed further below. In addition, support arms 16a, 16b are preferably integrally related to headband 12, with headband 12 and support arms 16a, 16b being made from a single piece of resilient polymeric material.

Coupled to first and second support arms 16a, 16b, respectively, are first 18a and second 18b resilient, curved hinge or fold regions. Hinge regions 18a, 18b are preferably U-shaped in configuration as shown. Hinge regions 18a, 18b are preferably integral with first and second support arms 16a, 16b and made from the same resilient material from which support arms 16a, 16b and headband 12 are fabricated.

First 20a and second 20b inner, head gripping recurve arms are coupled to first and second hinge regions 18a, 18b, respectively. Recurve arms 20a, 20b include inward facing, slightly curved head gripping regions 22a, 22b, respectively, with head gripping regions 22a, 22b structured and configured to comfortably engage a wearer's head. Recurve arms 20a, 20b are generally spaced apart from each other as shown to accommodate a wearer's head therebetween, and are slightly spaced apart from first and second support arms 16a, 16b respectively. In addition, recurve arms 20a, 20b terminate in forwardly disposed tips 24a, 24b, which are curved or turned slightly outward. Note that recurve arms 20a, 20b fold back toward bill 14. Preferably, the curvature of gripping regions 22a, 22b follows the curvature of support arms 16a, 16b so that the gripping regions and support arms are generally parallel.

Headband 12, first and second support arms, 16a, 16b, first and second hinge regions 18a, 18b, and first and second recurve arms 20a, 20b are preferably integral portions of a single piece and are fabricated from the same resilient, polymeric material such as polypropylene. Thus, first and second support arms 16a, 16b as well as first and second recurve arms 20a, 20b will resiliently respond to applied force. Generally, in a relaxed position, first and second support arms 16a, 16b have a pincer-like arrangement as shown in FIG. 3, and first and second recurve arms 20a, 20b are structured and configured such that first and second inner members are separated from each other by a distance which is slightly less than the diameter of a wearer's head. To use recurve visor 10, a wearer applies a slight force to first and second support arms 16a, 16b, which are in an opposing, pincer-like arrangement as mentioned above, to move first and second support arms 16a, 16b apart or away from each other and into a stressed position so that the wearer's head will fit between first and second recurve arms 20a, 20b. Upon releasing or removing the force from first and second support arms 16a, 16b, the arms move back towards their relaxed position, and apply a force to the wearer's head via first and second recurve arms 20a, 20b. The force applied by first and second support arms 16a, 16b to first and second recurve arms 20a, 20b, and thus to first and second head gripping regions 22a, 22b, provides for retention of visor 10 on a wearer's head.

First support arm 16a, hinge region 18a, and recurve arm 20a generally work together, as do second support arm 16b, hinge region 18b, and recurve arm 20b, to perform a spring-like function whereby tensional force applied by support arms 16a, 16b to a wearer's head is spread out along the length of curved head gripping regions 22a, 22b on recurve arms 20a, 20b. Thus, the tensional force applied to the wearer's head by first and second support arms 16a, 16b is spread out over the relatively large area provided by first and second head gripping regions 22a, 22b on first and second recurve arms 20a, 20b. The spreading out of the force applied by first and second support arms 16a, 16b to a wearer's head as described above provides for greater wearer comfort than is available in background art head visors.

Referring to FIG. 3, the space between first support arm 16a and first recurve arm 20a, and the space between second support arm 16b and second recurve arm 20b, provide first 26a and second 26b ventilation regions for allowing air circulation near the wearer's head, as well as allow for compression of gripping regions 22a, 22b to fit the wearer's head. The wearer can place his or her hair outside of first and second support arms 16a, 16b while wearing visor 10, so that the aforementioned air circulation in ventilation regions 26a, 26b between first and second support arms 16a, 16b and first and second recurve arms 20a, 20b, respectively, provides cooling and reduces perspiration by the wearer which may result in discomfort. The placing of the wearer's hair outside of first and second support arms 16a, 16b while wearing visor 10 additionally has the effect of providing a fuller look or appearance to the wearer's hair.

Accordingly, it will be seen that the present invention provides a head worn visor which allows increased wearer comfort for extended periods of time, and which reduces wearer perspiration which may result in discomfort. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. A recurve visor apparatus, comprising:
   (a) a headband;
   (b) a bill, said bill coupled to said headband;
   (c) a pair of outer arms, each said outer arm having a proximal end and a distal end, said outer arms coupled to said headband at said proximal ends; and
   (d) a pair of inner arms, each said inner arm having a proximal end and a distal end;
   (e) wherein the distal end of each said inner arm is coupled to the distal end of a corresponding outer arm by a resilient hinge section and wherein the proximal end of each said inner arm is spaced-apart from said corresponding outer arm, said hinges forming distal terminations of said inner and outer arms.

2. An apparatus as recited in claim 1, wherein each of said inner arms includes an arcuate head gripping region.

3. An apparatus as recited in claim 1, wherein said inner arms are spaced apart from said outer arms.

4. An apparatus as recited in claim 1, wherein said hinge regions are substantially U-shaped.

5. An apparatus as recited in claim 1, further comprising ventilation regions between said inner and outer arms.

6. A head visor, comprising:
   (a) a headband;
   (b) a proximally disposed bill, said bill coupled to said headband;
   (c) first and second resilient outer arms, said first and second outer arms having proximal ends connected to said headband;
   (d) first and second resilient, curved hinge regions, said first hinge region coupled to a distal end of said first outer arm, said second hinge region coupled to a distal end of said second outer arm; and
   (e) first and second inner head gripping recurve arms, said first inner recurve arm coupled to said first hinge region and said second inner recurve arm coupled to said second hinge region wherein said hinge regions form distal terminations of said inner and outer arms, said first inner recurve arm having a proximal end spaced apart from said first outer arm, said second inner recurve arm having a proximal end spaced apart from said second outer arm.

7. A head visor as recited in claim 6, wherein said first and second inner recurve arms each include a curved head gripping region.

8. A head visor as recited in claim 7, wherein said first and second inner recurve arms each include a forwardly disposed tip.

9. A head visor as recited in claim 7, wherein said hinge regions are substantially U-shaped.

10. A head visor as recited in claim 7, further comprising a first ventilation region between said first support arm and said first inner recurve arm, and a second ventilation between said second support arm and said second inner recurve arm.

11. A head visor apparatus, comprising:
   (a) a headband;
   (b) a bill coupled to said headband;
   (c) first and second outer support arms extending distally away from said headband;
   (d) first and second resilient, curved hinge regions, said first hinge region coupled to said first outer support arm, said second hinge region coupled to said second outer support arm; and
   (e) first and second inner head gripping recurve arms, said first inner recurve arm coupled to said first hinge region, said second inner recurve arm coupled to said hinge region;
   (f) wherein said support arms and said inner recurve arms terminate distally at said hinge regions and wherein said inner arms have proximal ends spaced-apart from said outer arms.

12. An apparatus as recited in claim 11, wherein said first and second inner recurve arms each includes a curved head gripping region.

13. An apparatus as recited in claim 11, wherein said first and second inner recurve arms each include a forwardly disposed tip.

14. An apparatus as recited in claim 13, wherein said hinge regions are substantially U-shaped.

15. An apparatus as recited in claim 13, further comprising a first ventilation region between said first support arm and said first inner recurve arm, and a second ventilation between said second support arm and said second inner recurve arm.

* * * * *